US010562922B2

United States Patent
Reddy et al.

(10) Patent No.: US 10,562,922 B2
(45) Date of Patent: Feb. 18, 2020

(54) SILICON BASED CYCLIC COMPOUNDS AND PHARMACEUTICAL COMPOSITIONS FOR TREATING MALARIA AND TOXOPLASMOSIS

(71) Applicant: Council of Scientific and Industrial Research, New Delhi (IN)

(72) Inventors: Dumbala Srinivasa Reddy, Pune (IN); Dhanasekaran Shanmugam, Pune (IN); Remya Ramesh, Pune (IN); Anurag Shukla, Pune (IN); Meenakshi Anil Belekar, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/999,537

(22) PCT Filed: Feb. 17, 2017

(86) PCT No.: PCT/IN2017/050067
§ 371 (c)(1),
(2) Date: Aug. 20, 2018

(87) PCT Pub. No.: WO2017/141272
PCT Pub. Date: Aug. 24, 2017

(65) Prior Publication Data
US 2019/0202843 A1    Jul. 4, 2019

(30) Foreign Application Priority Data
Feb. 19, 2016  (IN) .............. 201611005767

(51) Int. Cl.
C07F 7/08      (2006.01)
A61P 31/04     (2006.01)
A61P 33/06     (2006.01)

(52) U.S. Cl.
CPC ........... *C07F 7/0816* (2013.01); *A61P 31/04* (2018.01); *A61P 33/06* (2018.01)

(58) Field of Classification Search
CPC .......... C07F 7/0816; A61P 33/06; A61P 31/04
USPC ....................................... 514/63
See application file for complete search history.

(56) References Cited

U.S. PATENT DOCUMENTS

2012/0196882 A1    8/2012  Raj et al.

FOREIGN PATENT DOCUMENTS

| GB | 2396863 A | 7/2004 |
| WO | WO-2014128724 A1 | 8/2014 |
| WO | WO-2014181357 A1 | 11/2014 |
| WO | WO-2017141272 A1 | 8/2017 |

OTHER PUBLICATIONS

"International Application No. PCT/IN2017/050067, International Search Report and Written Opinion dated Jul. 17, 2017", (Jul. 17, 2017), 11 pgs.
Kamau, Edwin, et al., "A Novel Benzodioxole-Containing Inhibitor of Toxoplasma gondii Growth Alters the Parasite Cell Cycle", Antimicrobial Agents and Chemotherapy, vol. 55, No. 12, Dec. 2011, p. 5438-5451, (Dec. 2011), 5438-5451.
Fischer, Markus, et al., "Synthesis of 4-Silapiperidine Building Blocks with N—H Groups Using the Staudinger Reaction", *Organometallics*, 32(23), (2013), 7181-7185.
Heinrich, Tilman, et al., "4-Silapiperidine and 4-silapiperidinium derivatives: syntheses and structural characterization"., *Journal of Organometallic Chemistry*, 690(1), (2005), 33-47.
Mills, John S., et al., "Exploitation of silicon medicinal chemistry in drug discovery", *Expert Opinion on Investigational Drugs*, 13(9), (2004), 1149-1157.
Roos, David S., et al., "Chapter 3: Molecular Tools for Genetic Dissection of the Protozoan Parasite *Toxoplasma gondii;*", *Methods in Cell Biology*, vol. 45, (1994), 27-63.

*Primary Examiner* — Kristin A Vajda
(74) *Attorney, Agent, or Firm* — Schwegman Lundberg & Woessner, P.A.

(57) ABSTRACT

The present invention discloses novel silicon incorporated cyclic compounds of formula I, Wherein $Ar^1$ and $Ar^2$ are individually selected from any aryl group which can be optionally substituted; X is selected from any inorganic anion such as halide, carbonate, sulfate, nitrate or any organic anion selected from acetate, tartarate, citrate, carbonate or organosulfonates such as tosylate, mesylate, triflate; $R^1$ and $R^2$ are individually selected from C1-C8 alkyl, cycloalkyl, aryl, heteroaryl, aralkyl, alkoxyalkyl, aminoalkyl, thioalkyl, haloalkyl or hydroxyalkyl. $R^1$ and $R^2$ together may form a ring which optionally may be substituted or may contain heteroatoms; a pharmaceutical composition comprising a therapeutically effective amount of compounds of general formula I, including geometrical isomers and/or salts thereof along with a drug and optionally along with a carrier or diluent or pharmaceutically acceptable excipient for treating malaria and toxoplasmosis.

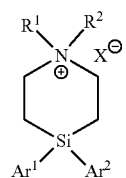

I

15 Claims, No Drawings

SILICON BASED CYCLIC COMPOUNDS AND PHARMACEUTICAL COMPOSITIONS FOR TREATING MALARIA AND TOXOPLASMOSIS

PRIORITY CLAIM TO RELATED APPLICATIONS

This application is a U.S. national stage filing under 35 U.S.C. § 371 from International Application No. PCT/IN2017/050067, filed on 17 Feb. 2017, and published as WO2017/141272 on 24 Aug. 2017, which claims benefit under 35 U.S.C. 119 to India Application No. 201611005767, filed on 19 Feb. 2016, the benefit of priority of each of which is claimed herein, and which applications and publication are hereby incorporated herein by reference in their entirety.

FIELD OF THE INVENTION

The present invention relates to novel silicon incorporated cyclic compounds. More particularly, the present invention relates to novel silicon incorporated cyclic compounds and pharmaceutical composition comprising novel silicon incorporated cyclic compounds for preventing, treating malaria and toxoplasmosis characterized by administering an effective dose of the pharmaceutical composition to a mammal.

BACKGROUND AND PRIOR ART OF THE INVENTION

Malaria is an infectious disease caused by the protozoan parasites belonging to *Plasmodium* genus and is transmitted to mammalian hosts through the bite of infected mosquitoes. Four species of *Plasmodium* are pathogenic in humans: *P. vivax*, *P. malariae*, *P. ovale*, and *P. falciparum*. Several other species of *Plasmodium* infect animals. According to WHO reports, 214 million cases were reported in 2015, and the annual deaths attributable to malaria stand at 500 thousand to 1 million cases. Most of the cases were reported from Sub Saharan African region (88%), followed by South-East Asia. However, attacks of malaria are rather increasing due to the increasing resistance of mosquitoes against insecticides and the appearance of genetic variants of parasites resistant to anti-malarial drugs. Although, several drugs are known to be effective in clinical treatment of malaria, the emergence and spread of drug resistance poses a big problem in current malaria treatment and elimination programs. The parasitic protozoan *Toxoplasma gondii* is the etiologic agent for toxoplasmosis, a parasitic disease widespread among various warm-blooded animals. Afflicted people mostly carry the infection lifelong, with the potential to flare-up or recrudesce under immunocompromised conditions, and hence *Toxoplasma* infections tend to be chronic in nature, primarily due to their ability to persist in the host as latent cysts. Treatment options for *Toxoplasma* include antibiotics such as clindamycin or pyrimethamine/sulphadoxin combination, but the effectiveness of these against the cyst form of the parasite is still not clear and hence it is quite difficult to clear infection completely from infected individuals. It is estimated that ~30% of the global population is infected by this pathogen, and is transmitted via the oral route by consumptions of contaminated food and water. Cats and other felines are primary hosts and can support sexual development of the parasite (akin to mosquitos in case of *Plasmodium*) and, the infectious forms of parasite (oocysts) are shed into the environment in cat feces. Clinical symptoms associated with *Toxoplasma* infection vary from severe (congenital encephalopathy in neonates) to mild (self limiting fever in healthy adults).

US 20120196882 A1 provides method of preventing or slowing the transmission of *Plasmodium* organisms between mammals by blocking oocyst formation and transmission of a *Plasmodium* parasite comprising administering to a mammal infected with malaria parasite or suspected of being infected with malaria parasite, artemisinin and one or two doses of ketotifen administered in doses of between 0.1 mg/kg and 0.5 mg/kg of ketotifen.

The Menshutkin reaction converts a tertiary amine to a quaternary ammonium salt by reaction with an alkyl halide. Source—Wikipedia

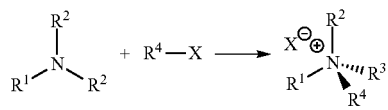

Article titled, "Synthesis of 4-Silapiperidine Building Blocks with N—H Groups Using the Staudinger Reaction" by Markus Fischer and Reinhold Tacke in *Organometallics*, 2013, 32 (23), pp 7181-7185 reports a novel acid-free method for the synthesis of 4-silapiperidine building blocks with N—H groups, using the Staudinger reaction as the key step.

Article titled, "4-Silapiperidine and 4-silapiperidinium derivatives: syntheses and structural characterization" by Tilman Heinrich, Christian Burschka, Martin Penka, Brigitte Wagner, Reinhold Tacke in Journal of Organometallic Chemistry, Volume 690, Issue 1, 3 Jan. 2005, Pages 33-47 reports a series of novel 4-silapiperidine and 4-silapiperidinium derivatives, with two silicon-bound aryl groups and various N-organyl groups, synthesized and structurally characterized. These investigations provide the basis for the development of novel silicon-based drugs containing a 4-silapiperidine or 4-silapiperidinium skeleton.

GB2396863 (A) discloses a compound of formula (I) R4 R1O/\ON/wherein R' is hydrogen or alkyl; R2 and R3 are the same or different and are each alkyl; R4 is hydrogen, halogen, alkyl, NO2 or CF3; and R5 and R6 are the same or different and are each hydrogen, alkyl, halogen or alkoxy; or a pharmaceutically acceptable salt thereof. These compounds are calcium (Ca<2+>) channel blockers. These compounds may be useful in the treatment of cardiovascular diseases such as cardiac arryhythmia, glaucoma or hypertension. A preferred compound is sila-niguldipine.

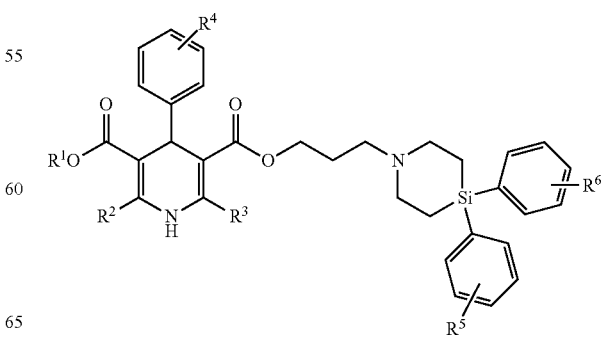

WO 2014128724 A1 discloses silicon analogs of piperine of formula A with increased antibacterial efficacy and their preparation thereof. Further, a compound of general formula A,

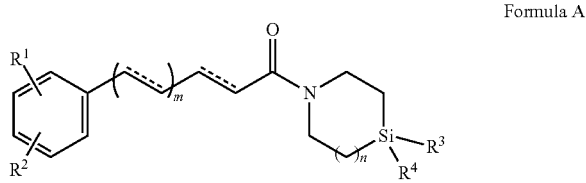

Formula A wherein $R^1$, $R^2$ each are individually selected from H, hydroxy, alkoxy or $R^1$ and $R^2$ may form alicyclic or aromatic ring which may additionally contain one or two hetero atoms; $R^3$, $R^4$ each are individually selected from alkyl, aryl, alkoxy, halo or $R^3$ and $R^4$ may form alicyclic ring which may additionally contain an hetero atom; m, n=0, 1, 2.

The search for new antimalarial drugs is still in progress. However, the hope that new drugs would help eradicate the disease has not been realized. Accordingly, what is needed in the art are new treatments for effectively combating malaria, and particularly malarial forms that are resistant to current treatments, but without the side-effects and complications of drugs and treatments that are presently available. Also there is an urgent need for new and effective drugs for treating and preventing chronictoxoplasmosis.

OBJECTS OF THE INVENTION

The main objective of the present invention is to provide novel silicon incorporated cyclic compounds and pharmaceutical composition comprising novel silicon incorporated cyclic compounds or pharmaceutically acceptable salt thereof.

Another objective of the present invention is to provide a pharmaceutical composition comprising novel silicon incorporated cyclic compounds for preventing, treating malaria and toxoplasmosis characterized by administering an effective dose of the pharmaceutical composition to a mammal.

SUMMARY OF THE INVENTION

Accordingly, the present invention provides novel silicon incorporated cyclic compounds of formula (I) and pharmaceutical composition comprising compounds of formula (I) or pharmaceutically acceptable salt thereof.

In an embodiment, the present invention provides novel silicon incorporated cyclic compounds of formula (I),

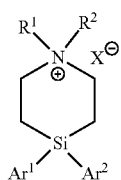

I

Wherein $Ar^1$ and $Ar^2$ are individually selected from any aryl group which can be optionally substituted;

X is selected from any inorganic anion such as halide, carbonate, sulfate, nitrate or any organic anion selected from acetate, tartarate, citrate, carbonate or organosulfonates selected from tosylate, mesylate ortriflate;

$R^1$ and $R^2$ are individually selected from C1-C8 alkyl, cycloalkyl, aryl, heteroaryl, aralkyl, alkoxyalkyl, aminoalkyl, thioalkyl, haloalkyl or hydroxyalkyl. $R^1$ and $R^2$ together may form a ring which optionally may be substituted or may contain heteroatoms;

or pharmaceutically acceptable salt thereof.

In another embodiment, the present invention provides a pharmaceutical composition comprising compounds of formula (I) and at least one pharmaceutically acceptable carrier.

In yet another embodiment, the present invention provides a pharmaceutical composition comprising compound of formula (I) or pharmaceutically acceptable salt thereof and at least one pharmaceutically acceptable carrier for preventing, treating malaria and toxoplasmosis characterized by administering an effective dose of the pharmaceutical composition to a mammal.

In a preferred embodiment, the present invention provides a pharmaceutical composition comprising compounds of formula (I) for the treatment of diseases caused by the pathogens *Plasmodium falciparum* and *Toxoplasma gondii*.

DETAILED DESCRIPTION OF THE INVENTION

The invention will now be described in detail in connection with certain preferred and optional embodiments, so that various aspects thereof may be more fully understood and appreciated.

In an embodiment, the present invention provides novel silicon incorporated cyclic compounds of formula (I),

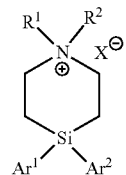

Formula (I)

Wherein $Ar^1$ and $Ar^2$ are individually selected from any aryl group which can be optionally substituted;

X is selected from any inorganic anion such as halide, carbonate, sulfate, nitrate or any organic anion selected from acetate, tartarate, citrate, carbonate or organosulfonates selected from tosylate, mesylate or triflate;

$R^1$ and $R^2$ are individually selected from C1-C8 alkyl, cycloalkyl, aryl, heteroaryl, aralkyl, alkoxyalkyl, aminoalkyl, thioalkyl, haloalkyl or hydroxyalkyl. $R^1$ and $R^2$ together may form a ring which optionally may be substituted or may contain heteroatoms;

or pharmaceutically acceptable salt thereof.

In another embodiment, the present invention provides a pharmaceutical composition comprising compound of formula (I),

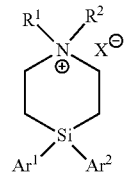

Formula (I)

Wherein Ar¹ and Ar² are individually selected from any aryl group which can be optionally substituted;

X is selected from any inorganic anion such as halide, carbonate, sulfate, nitrate or any organic anion selected from acetate, tartarate, citrate, carbonate or organosulfonates selected from tosylate, mesylate ortriflate;

R¹ and R² are individually selected from C1-C8 alkyl, cycloalkyl, aryl, heteroaryl, aralkyl, alkoxyalkyl, aminoalkyl, thioalkyl, haloalkyl or hydroxyalkyl. R¹ and R² together may form a ring which optionally may be substituted or may contain heteroatoms;

or pharmaceutically acceptable salt thereof.

In another embodiment, the present invention provides a pharmaceutical composition comprising one or more compounds of formula (I),

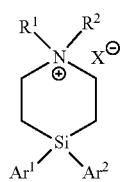

Formula (I)

Wherein Ar¹ and Ar² are individually selected from any aryl group which can be optionally substituted;

X is selected from any inorganic anion such as halide, carbonate, sulfate, nitrate or any organic anion selected from acetate, tartarate, citrate, carbonate or organosulfonates-selected from tosylate, mesylate ortriflate;

R¹ and R² are individually selected from C1-C8 alkyl, cycloalkyl, aryl, heteroaryl, aralkyl, alkoxyalkyl, aminoalkyl, thioalkyl, haloalkyl or hydroxyalkyl. R¹ and R² together may form a ring which optionally may be substituted or may contain heteroatoms;

or pharmaceutically acceptable salt thereof.

In a preferred embodiment, the present invention provides a pharmaceutical composition comprising the compound of formula (I) or pharmaceutically acceptable salt thereof, wherein the compound of formula (I) is selected from

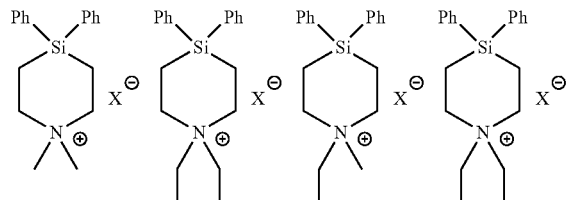

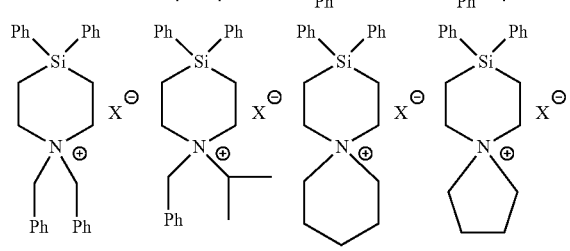

-continued

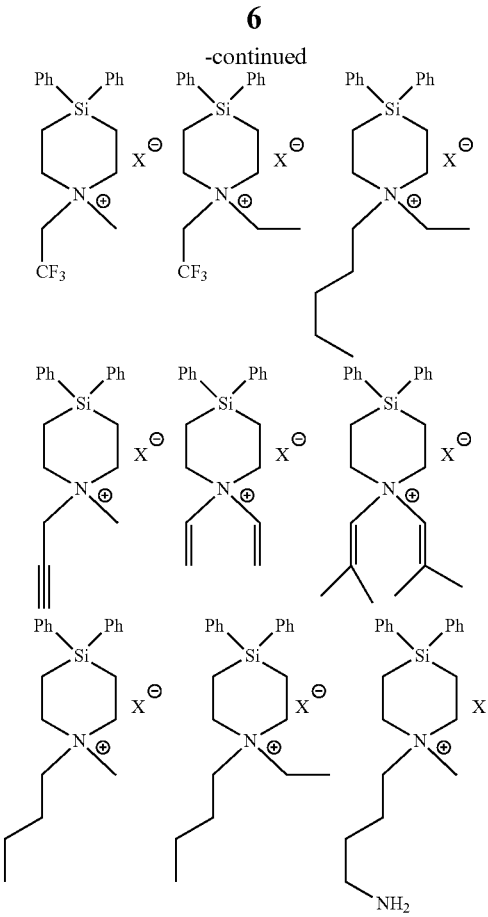

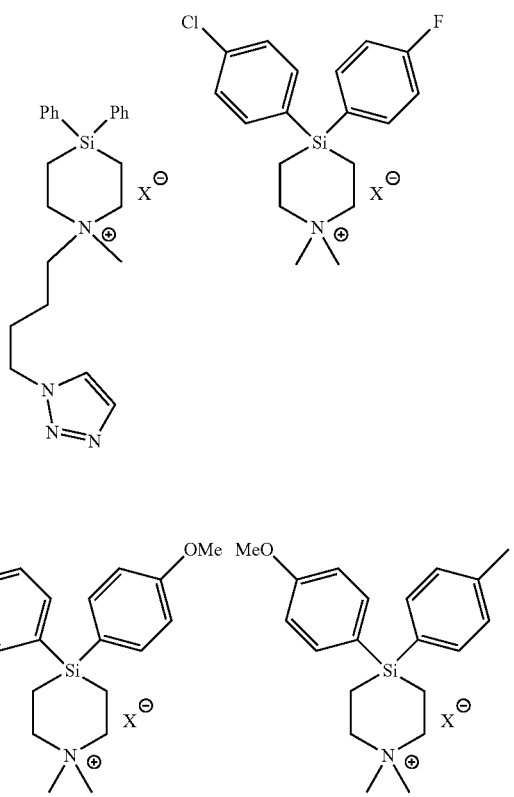

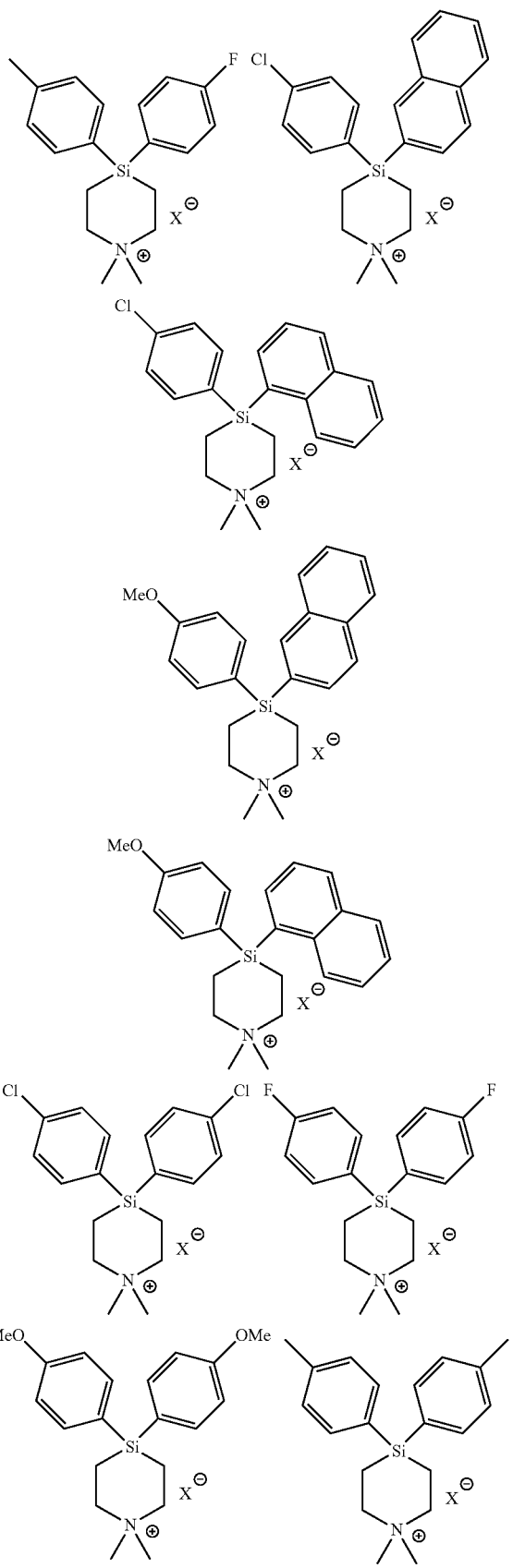

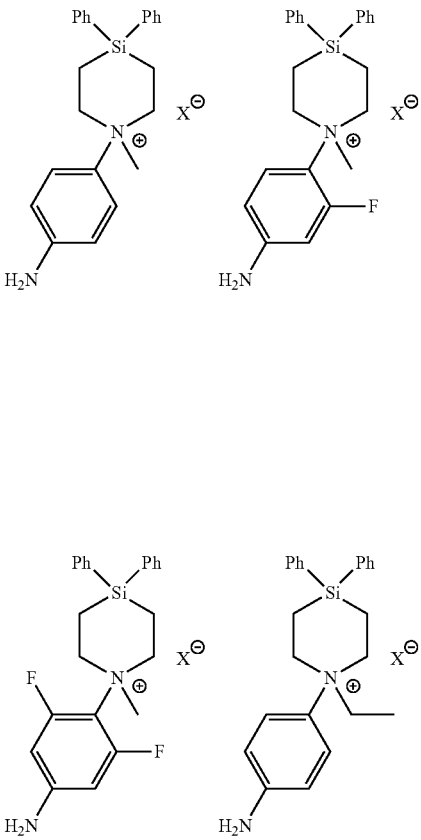

Wherein X may be any inorganic anion such as halide, carbonate, sulfate, nitrate or any organic anion selected from acetate, tartarate, citrate or organosulfonates such as tosylate, mesylate, triflate.

In another embodiment of the present invention, there is provided a pharmaceutical composition as described herein, wherein said composition comprises the compound of formula (I) or pharmaceutically acceptable salt thereof in the range of 1 to 25% by weight In yet another embodiment, the present invention provides a process for preparation of t compounds of the general formula (I), wherein said process comprises the step of treating the tertiary amine precursor with the corresponding organic partner.

The above process is shown below in Scheme 1:

Scheme: 1

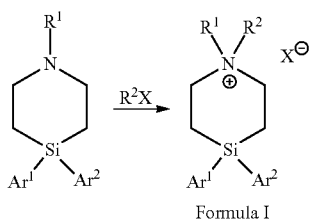

The biological activity of selected compounds is shown below in Table 1.

TABLE 1

| Sample Code | Structure | % inhibition (T. gondii) | IC$_{50}$ (T. gondii, μM) | % inhibition (P. falciparum) | IC$_{50}$(P. falciparum, μM) |
|---|---|---|---|---|---|
| NDS 100860 | 4,4-diphenyl-1-benzylpiperidine-silicon, HCl | 99.36 | 5.03/2.09 | 111.7 | 1.75/2.30 |
| NDS 100861 (2) | 4,4-diphenyl-1-methyl-1-benzyl silinane, I | 36.0 | ND | 114.6 | 1.64/2.39 |
| NDS 100952 (3) | 4,4-diphenyl-1,1-dibenzyl silinanium, Br$^-$ | 72.06 | 1.24 | 104.01 | 0.33 |
| NDS 100953 (4) | 4,4-diphenyl-1-ethyl-1-benzyl silinanium, I$^-$ | 39 | ND | 94.96 | 1.69 |
| NDS 101017 (5) | 4,4-diphenyl-spiro silinane-piperidinium, Br$^-$ | 0.00 | ND | 87.07 | 2.07/4.98 |
| NDS 101044 (7) | 4,4-diphenyl-1,1-dimethyl silinanium, I$^-$ | 0.00 | ND | 63.50 | 2.46 |
| NDS 101039 (8) | 4,4-diphenyl-1-methyl-1-allyl silinanium, Br$^-$ | 17.00 | ND | 76.23 | 7.11 |

TABLE 1-continued

| Sample Code | Structure | % inhibition (T. gondii) | IC₅₀ (T. gondii, µM) | % inhibition (P. falciparum) | IC₅₀(P. falciparum, µM) |
|---|---|---|---|---|---|
| NDS 101015 (9) | [structure] | 20.00 | ND | 103.48 | 0.48/0.29 |

In still another embodiment, the present invention provides a pharmaceutical composition comprising compound of formula (I) or pharmaceutically acceptable salt thereof and at least one pharmaceutically acceptable carrier.

The carrier is typically used when the composition is prepared, and includes, but not limited to, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talcum, magnesium stearate, mineral oil, or the like.

The composition can additionally comprise an antiseptic, stability improving material, viscosity improving or adjusting material, solubility improving material, sweetener, dye, palatability improving material, osmotic pressure variable salt, buffer solution, antioxidant, and so on.

In an embodiment of the present disclosure there is provided a pharmaceutical composition as described herein, wherein the composition is adapted for oral, systematic or topical administration The pharmaceutical compositions of the present invention can be oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

In the present invention, the pharmaceutically acceptable salt can include a pharmaceutically acceptable acid addition salt. The pharmaceutically acceptable acid addition salt can be obtained from inorganic acids such as hydrochloric acid, nitric acid, sulfuric acid, hydrobromic acid, hydroiodic acid, nitrous acid, or phosphorous acid, and nontoxic organic acids such as aliphatic mono- and di-carboxylates, phenyl-substituted alkanoate, hydroxyl alkanoate, and alkandioate, aromatic acids, and aliphatic and aromatic sulfuric acids. More specifically, examples of the pharmaceutically acceptable acid addition salt can include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acylate, formate, isobutyrate, caprate, heptanoate, propiolate, oxalate, malonate, succinate, suberate, sebacate, fumarate, maleate, butyne-1, 4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenylacetate, phenylpropionate, phenylbutyrate, citrate, lactate, -hydroxybutyrate, glycolate, maleate, tartrate, methane sulfonate, propane sulfonate, naphthalene-1-sulfonate, naphthalene-2-sulfonate or mandelate.

In another embodiment, the present invention provides a pharmaceutical composition comprising compound of formula (I) or pharmaceutically acceptable salt thereof for preventing and treating malaria and toxoplasmosis comprising administering an effective dose of the pharmaceutical composition to a mammal.

In a preferred embodiment, the present invention provides a pharmaceutical composition comprising compounds of formula (I) or pharmaceutically acceptable salt thereof for the treatment of diseases caused by the pathogens *Plasmodium falciparum* and *Toxoplasma gondii*.

Further, the present invention provides a method of treating mammalian malaria, which is characterized by administering an effective dose of pharmaceutical composition to a mammal.

Typically, the pharmaceutical composition is administered in the form of a unit dose containing its effective ingredient at an amount between about 1 mg and about 50 mg. The total dose per day of the inventive pharmaceutical composition is within a range from about 1 mg to about 50 mg, and preferably from about 1 mg to about 30 mg. However, in comprehensive consideration of the situation of a patient, and in consideration of the activity of an administered medication, a specific dose beyond such a range can be administered. An optimal dose administered under a specific situation must be decided experimentally.

The compounds can be administered once or several times at a dose. Preferably, a dose per day is administered once or twice per day. The inventive compounds can be administered alone or in conjunction with a pharmaceutically acceptable carrier and excipient. The inventive pharmaceutical composition can be formulated into excipient known in the art as well as a pharmaceutically acceptable carrier and diluents. This formulation can take the form of a unit dose by a method known in the pharmaceutical field for convenience.

The pharmaceutical composition is used in conjunction with one or more other therapeutically useful materials, for instance other anti-malarial drugs.

US 20120196882 A1 provides method of preventing or slowing the transmission of *Plasmodium* organisms between mammals by blocking oocyst formation and transmission of a *Plasmodium* parasite comprising administering to a mammal infected with malaria parasite or suspected of being infected with malaria parasite, artemisinin and one or two doses of ketotifen administered in doses of between 0.1 mg/kg and 0.5 mg/kg of ketotifen.

But, the present invention provides compounds and its composition belonging to a completely different class having anti-malarial and anti-toxoplasmal activity.

In an embodiment of the present invention there is provided a method of treating infections comprising administrating to a subject in need of such treatment a therapeutically effective amount of pharmaceutical composition of compound of formula I, including its geometrical isomers, its analogues and/or salts thereof as claimed in claim 1, along with the drug and optionally along with a carrier or diluent or pharmaceutically acceptable excipient.

In yet another embodiment of the present disclosure, there is provided a method of treating infections as described herein, wherein the infection caused by a bacteria that employs an efflux pump resistance as one of the ways of resistance, comprising administering to a patient in need thereof a therapeutically effective amount of an antibacterial agent and a compound of formula I, including its geometrical isomers, its analogues or and salts thereof.

EXAMPLES

Following examples are given by way of illustration therefore should not be construed to limit the scope of the invention.

Example 1

1-benzyl-1-methyl-4,4-diphenyl-1λ4,4-azasilinan-2-ylium iodide (2)

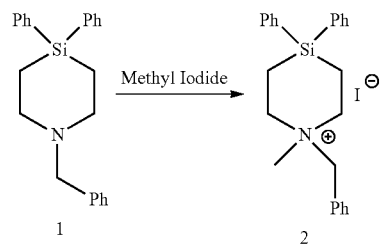 [SMILES: c1ccc(CN2CC[Si](c3ccccc3)(c3ccccc3)CC2)cc1 ; C[N+]1(Cc2ccccc2)CC[Si](c2ccccc2)(c2ccccc2)CC1 ; [I-]]

The compound 1 was prepared by following procedures known in the literature (*J. Organomet. Chem.* 2005, 690, 33-47). Compound 1 (100 mg) was stirred with Methyl iodide (3 mL) at R.T overnight. Methyl iodide was evaporated in a rotavapor to give the product as a yellow solid (78 mg). $^1$H NMR (400 MHz, CDCl$_3$) δ 7.76-7.32 (m, 15H), 5.05 (s, 2H), 4.09 (m, 2H), 3.69 (m, 2H), 3.30 (s, 3H), 1.68 (m, 4H); $^{13}$C NMR (100 MHz, CDCl$_3$) δ 134.2, 134.1, 133.2, 131.2, 130.5, 130.43, 130.38, 128.9, 128.5, 128.3, 126.5, 67.4, 59.8, 45.7, 6.7

Example 2

1-benzyl-1-ethyl-4,4-diphenyl-1λ4,4-azasilinan-2-ylium iodide (3)

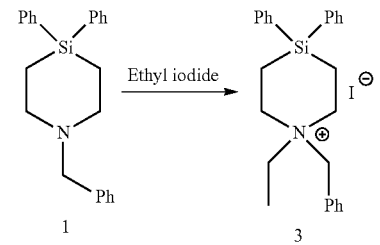 [SMILES: c1ccc(CN2CC[Si](c3ccccc3)(c3ccccc3)CC2)cc1 ; CC[N+]1(Cc2ccccc2)CC[Si](c2ccccc2)(c2ccccc2)CC1 ; [I-]]

Compound 3 was prepared from compound 1 and ethyl iodide by employing similar procedure described for the synthesis of 2. $^1$H NMR (400 MHz, CDCl$_3$) δ 7.58-7.34 (m, 15H), 4.76 (s, 2H), 3.91 (m, 2H), 3.60 (q, J=7.1 Hz, 2H), 3.50 (m, 2H), 1.66 (m, 4H), 1.51 (t, J=7.3 Hz, 3H); $^{13}$C NMR (100 MHz, CDCl$_3$) δ 134.2, 133.2, 131.6, 130.8, 130.7, 130.5, 129.2, 128.7, 128.6, 126.7, 63.2, 56.7, 52.4, 7.9, 6.7.

Example 3

1,1-dibenzyl-4,4-diphenyl-1λ4,4-azasilinan-2-ylium bromide (4)

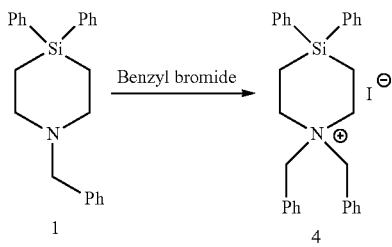 [SMILES: c1ccc(CN2CC[Si](c3ccccc3)(c3ccccc3)CC2)cc1 ; c1ccc(C[N+]2(Cc3ccccc3)CC[Si](c3ccccc3)(c3ccccc3)CC2)cc1 ; [I-]]

Compound 4 was prepared from compound 1 and benzyl bromide by employing similar procedure described for the synthesis of 2. $^1$H NMR (400 MHz, CDCl$_3$) δ 7.67 (m, 4H), 7.42-7.34 (m, 16H), 5.07 (s, 2H), 3.85 (m, 4H), 1.81 (m, 4H); $^{13}$C NMR (100 MHz, CDCl$_3$) δ 134.1, 133.2, 130.9, 130.8, 130.6, 129.2, 128.6, 126.9, 62.9, 56.0, 7.2.

Example 4

3,3-diphenyl-6λ$^4$-aza-3-silaspiro[5.5]undecan-7-ylium bromide (5)

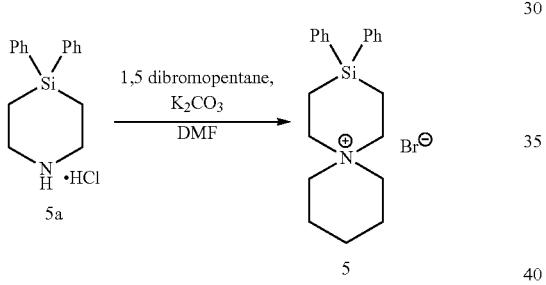

The compound 5a was prepared according to known procedures (WO2013/054275). Compound 5a (30 mg) was stirred with 1,5-dibromopentane (15 μL) and K$_2$CO$_3$ (63 mg) in DMF (4 mL) at overnight, solvent was evaporated on rotavepor to give the product as white solid (28 mg). $^1$H NMR (400 MHz, CDCl$_3$) δ7.52 (m, 4H), 7.49-7.35 (m, 6H), 3.90 (m, 4H), 3.82 (m, 4H), 1.92 (m, 6H), 1.63 (m, 4H); $^{13}$C NMR (100 MHz, CDCl$_3$) δ134.3, 131.1, 130.8, 128.7, 77.3, 76.7, 59.1, 58.4, 20.6, 19.9, 6.0.

Example 5

1,1-dimethyl-4,4-diphenyl-1,4-azasilinan-1-ium iodide (7)

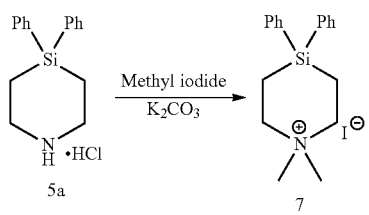

Compound 5a (30 mg) was stirred with methyl iodide (1 mL) and K$_2$CO$_3$ (15 mg) at overnight, then reaction mixture was filtered to remove K$_2$CO$_3$ and washed with DCM. The filtrate was evaporated on rotavapor to give the product as white solid (25 mg). $^1$H NMR (400 MHz, CDCl$_3$) δ 7.58-7.47 (m, 4H), 7.47-7.34 (m, 6H), 3.87 (m, 4H), 3.49 (d, J=8.3 Hz, 6H), 1.68 (m, 4H); $^{13}$C NMR (100 MHz, CDCl$_3$) δ 134.3, 130.8, 130.7, 128.6, 63.3, 51.8, 7.1.

Example 6

1-allyl-1-methyl-4,4-diphenyl-1,4-azasilinan-1-ium bromide (8)

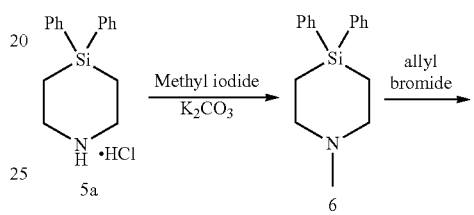

Compound 5a (30 mg) was stirred with methyl iodide (18 μL) and K$_2$CO$_3$ (15 mg) at overnight, then reaction mixture was filtered to remove K$_2$CO$_3$ and washed with DCM, filtrate was evaporated on rotavepor to give the crude product as white solid (22 mg). and crude product was diluted with allyl bromide (1.5 mL) and stirred at 6 hours, solvent was evaporated on rotavepor to give the product as white solid (28 mg)$^1$H NMR (400 MHz, CDCl$_3$) δ 7.61-7.32 (m, 10H), 6.11-5.85 (m, 2H), 5.73 (d, J=8.8 Hz, 1H), 4.49-4.36 (m, 2H), 3.90 (dd, J=6.1, 12.5 Hz, 2H), 3.82-3.64 (m, 2H), 3.43-3.27 (br, s, 3H), 1.70 (m, 4H); $^{13}$C NMR (100 MHz, CDCl$_3$) δ 134.4, 130.9, 130.7, 130.4, 128.8, 128.7, 123.7, 77.3, 76.7, 64.9, 60.6, 48.2, 6.9.

Example 7

1,1-bis(3-methylbut-2-en-1-yl)-4,4-diphenyl-1,4-azasilinan-1-ium bromide (9)

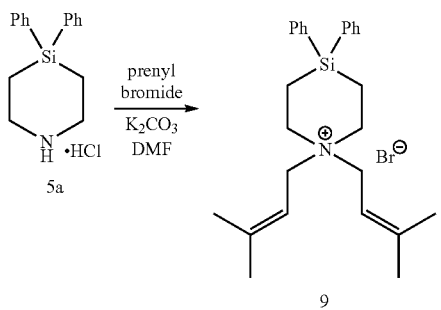 [SMILES: c1ccc([Si]2(c3ccccc3)CCNCC2)cc1 ; Cl ; CC(C)=CC[N+]1(CC=C(C)C)CC[Si](c2ccccc2)(c2ccccc2)CC1 ; [Br-]]

Compound 5a (30 mg) was stirred with 3,3-Dimethylallyl bromide (2 mL) and $K_2CO_3$ (43 mg) at overnight, then reaction mixture evaporated on rotavepor to give the product as (24 mg). $^1$H NMR (200 MHz, $CDCl_3$) δ=7.64-7.39 (m, 10 H), 5.33-5.20 (m, 2 H), 4.31 (d, J=8.0 Hz, 3 H), 3.82 (t, J=6.7 Hz, 3 H), 1.94 (s, 6 H), 1.87 (s, 7 H), 1.72 (t, J=6.5 Hz, 4 H).

Example 8

Protocol for Anti-malarial and Anti-toxoplasma Bioactivity Screening a) Anti-malarial Screening:

*Plasmodium falciparum* (3D7; Malaria Research and Reference Reagent Resource Center ID NO: MRA-102) is cultured in the laboratory as per standard protocols [Moll K., Ljungström I., Perlmann H., Scherf A., and Wahlgren M., (Editors). Methods in Malaria Research. Joint publication by Malaria Research and Reference Reagent Resource Center (MR4), ATCC, USA and BioMalPar, EU. 2008]. Briefly, *P. falciparum* is cultured using 2% hematocrit washed RBCs, separated from freshly collected human blood, in RPMI media containing glutamine, sodium bicarbonate and antibiotics. Parasites are routinely synchronized using 5% sorbitol treatment. Anti-malarial screens are carried out in two stages: 1) a primary screen at a fixed concentration of 10 μM to find out % inhibition of growth; and 2) a dose assay for finding out the $IC_{50}$ for hits identified from the primary screen. Assays are setup as follows. 200 μls of the diluted parasite culture (2% parasitemia and 2% hematocrit; at late ring stage), is added to each well in a 96 well plate pre-seeded with the compound of interest at the required concentration of 10 μM. The master stocks and dilutions of the compounds are prepared in cell culture grade DMSO. NOTE: DMSO only treatment control is done and the results are used for normalizing the data obtained from compound treatment. All compounds are plated in triplicates. Each 96 well plate also includes negative controls (compound untreated culture) and positive controls (standard anti-malarial treated culture). Standard anti-malarials used are chloroquine, artemisinine and atovaquone, each at 1 μM concentration. After plating, the culture is incubated in standard growth condition for 60 hours, after which the cultures are processed for testing the effect of compounds on parasite growth using SybrGreen staining and fluorescence measurements at 520 nM emmission following excitation at 498 nM. Since only parasites have DNA (as RBCs are devoid of nucleus), the SybrGreen signal is a direct indictor of parasitemia in respective samples. Results are used to quantifying relative parasite growth (or conversely % inhibition of growth) in untreated, standard anti-malarial treated and test molecule treated *P. falciparum* cultures. Compounds showing greater than 80% reduction in parasitemia are selected for dose response analysis and $IC_{50}$ determination using the respective test molecules in a dilution series ranging from 10 μM to 1 nM. Data from the preliminary screen (@ 10 μM only) along with data from the dose response experiment and $IC_{50}$ values for the selected molecules are tabulated in Table-2.

b) Anti-toxoplasma Screening:

For screening bioactivity of test molecules against *T. gondii*, a transgenic line of the parasite (TgLuc+) expressing the luciferase gene is used [Edwin Kamau, Tracy Meehan, Mark D. Lavine, Gustavo Arrizabalaga, Gabriela Mustata Wilson and Jon Boyle. A Novel Benzodioxole-Containing Inhibitor of *Toxoplasmagondii* Growth Alters the Parasite Cell Cycle. Antimicrob Agents Chemother. 2011, 55(12): 5438-5451]. The parental parasite used to generate the TgLuc+ strain is aType I (RH) virulent strain (ATCC reference 50174D), which can also be used for in vivo studies in mice, if needed. The tachyzoite stage of the parasites are routinely cultured in the laboratory using standard protocols [Roos D S, Donald R G, Morrissette N S, Moulton A L. Molecular tools for genetic dissection of the protozoan parasite *Toxoplasma gondii*. Methods Cell Biol. 1994, 45:27-63]. In brief, a confluent monolayer of Human Foreskin Fibroblast (HFF; ATCC reference SCRS-1041) cells in culture are used as the host cells for infection with tachyzoitestage *T. gondii*. The culture media used to grow parasites is standard complete DMEM (Gibco BRL, USA) containing glucose (5.5 mM), glutamine (2 mM), Hepes (25 mM) and 1% dialyzed bovine fetal calf serum (Gibco BRL, USA). For bioactivity assays, the HFF cells are grown in 96 well plates and each well is infected with $1\times10^4$TgLuc+parasitesin the presence of 10 μM test molecules (in primary screens) in a total volume of 200 μL. After 2 days of incubation and growth in a 37° C. incubator maintaining 5% $CO_2$, the 96 well plates are processed for luminescence measurements using the reagents in the luciferase assay kit (Promega, USA). The results are corrected for background (uninfected HFF cultures), and normalized against both positive (untreated parasite cultures) and negative (standard drug treated parasite cultures) to identify those molecules with % inhibition values >80% for further dose analysis and $IC_{50}$ determination using a dilution series ranging from 10 μM to 1 nM. Data from the preliminary screen (@ 10 μM only) is shown in Table-1 and dose response experiments are underway.

Biological activity of selected compounds is given below.

TABLE 1

| Sample Code | Structure | % inhibition (T. gondii) | IC$_{50}$ (T. gondii, μM) | % inhibition (P. falciparum) | IC$_{50}$(P. falciparum, μM) |
|---|---|---|---|---|---|
| NDS 100860 | (Ph,Ph-Si piperidine, N-CH2Ph, HCl) | 99.36 | 5.03/2.09 | 111.7 | 1.75/2.30 |
| NDS 100861 (2) | (Ph,Ph-Si piperidine, N-Me, N-CH2Ph, I) | 36.0 | ND | 114.6 | 1.64/2.39 |
| NDS 100952 (3) | (Ph,Ph-Si piperidine, N+(CH2Ph)2, Br−) | 72.06 | 1.24 | 104.01 | 0.33 |
| NDS 100953 (4) | (Ph,Ph-Si piperidine, N+(Et)(CH2Ph), I−) | 39 | ND | 94.96 | 1.69 |
| NDS 101017 (5) | (Ph,Ph-Si piperidine, spiro N+ piperidine, Br−) | 0.00 | ND | 87.07 | 2.07/4.98 |
| NDS 101044 (7) | (Ph,Ph-Si piperidine, N+Me2, I−) | 0.00 | ND | 63.50 | 2.46 |
| NDS 101039 (8) | (Ph,Ph-Si piperidine, N+Me(allyl), Br−) | 17.00 | ND | 76.23 | 7.11 |

TABLE 1-continued

| Sample Code | Structure | % inhibition (T. gondii) | IC$_{50}$ (T. gondii, µM) | % inhibition (P. falciparum) | IC$_{50}$(P. falciparum, µM) |
|---|---|---|---|---|---|
| NDS 101015 (9) | Ph-Si-Ph ring with N⁺ Br⁻, two prenyl groups | 20.00 | ND | 103.48 | 0.48/0.29 |

Example 9

| Drug | 10.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Then the active ingredient and Magnesium stearate was mixed and filled in a sample vial.

Mode of administration: Disperse the powder in water/juice.

Example 10

| Drug | 10.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Then the active ingredient and Magnesium stearate was mixed and filled in a sample vial.

Mode of administration: Disperse the powder in water/juice.

Example 11

| Compound | 10.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Mix active ingredient and Magnesium stearate and may be filled in a capsule of suitable size.

Mode of administration: The capsule may be had with water of juice.

Example 12

| Compound | 20.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Mix active ingredient and Magnesium stearate and may be filled in a capsule of suitable size.

Mode of administration: The capsule may be had with water of juice.

Example 13

| Compound | 10.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Mix active ingredient and Magnesium stearate and may be filled in a capsule of suitable size.

Mode of administration: The tablet may be had with water of juice.

Example 14

| Compound | 5.0% w/w |
|---|---|
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour.

Water was evaporated on rotary vapour to adsorb colour and flavour on mannitol. Mix active ingredient and Magnesium stearate and may be compressed as tablet. Mode of administration: The tablet may be had with water of juice.

Example 15

| Compound | 10.0% w/w |
| Colour Iron oxide red | 0.3% w/w |
| Strawberry Flavour | 0.7% w/w |
| Magnesium stearate | 2.0% w/w |
| Mannitol | q.s. to 100.0% w/w |

Procedure: Dissolve mannitol in 2.0 ml of water. Then iron oxide red was added followed by strawberry flavour. Water was evaporated on rotary vapour to adsorb colour and flavour on mannitol. Mix active ingredient and Magnesium stearate and fill in pouch or bottle. Mode of administration: Disperse the powder in water/juice.

Advantages of the Invention:
a. Novel compounds
b. Compositions comprising disclosed compounds are useful in treating diseases caused by the pathogens *Plasmodium falciparum* and *Toxoplasma gondii*.

We claim:
1. Silicon based cyclic compounds of formula I,

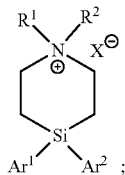

I wherein
Ar$^1$ and Ar$^2$ are individually selected from any aryl group which can be optionally substituted;
X is selected from any inorganic anion and any organic anion;
R$^1$ and R$^2$ are individually selected from C1-C8 alkyl, cycloalkyl, aryl, heteroaryl, aralkyl, alkoxyalkyl, aminoalkyl, thioalkyl, haloalkyl or hydroxyalkyl, or R$^1$ and R$^2$ together may form a ring which optionally may be substituted or may contain heteroatoms;
or a geometrical isomer, analogue, or a pharmaceutically acceptable salt thereof.

2. A pharmaceutical composition comprising a therapeutically effective amount of one or more compounds of general formula I, or a geometrical isomer, analogue and/or salt thereof,

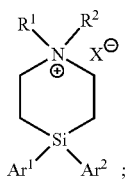

I wherein
Ar$^1$ and Ar$^2$ are individually selected from any aryl group which can be optionally substituted;
X is selected from any inorganic anion and any organic anion;
R$^1$ and R$^2$ are individually selected from C1-C8 alkyl, cycloalkyl, aryl, heteroaryl, aralkyl, alkoxyalkyl, aminoalkyl, thioalkyl, haloalkyl or hydroxyalkyl, R$^1$ and R$^2$ together may form a ring which optionally may be substituted or may contain heteroatoms;
along with a carrier or diluent or pharmaceutically acceptable excipient.

3. The pharmaceutical composition as claimed in claim 2, wherein one or more of the compounds of general formula I are in the form of a salt, wherein the salt is a pharmaceutically acceptable salt selected from hal, organosulfonates, acetate, succinate, and maleate.

4. The pharmaceutical composition as claimed in claim 2, wherein said composition comprises the compound of formula I or pharmaceutically acceptable salt thereof, wherein the compound of formula I is selected from:

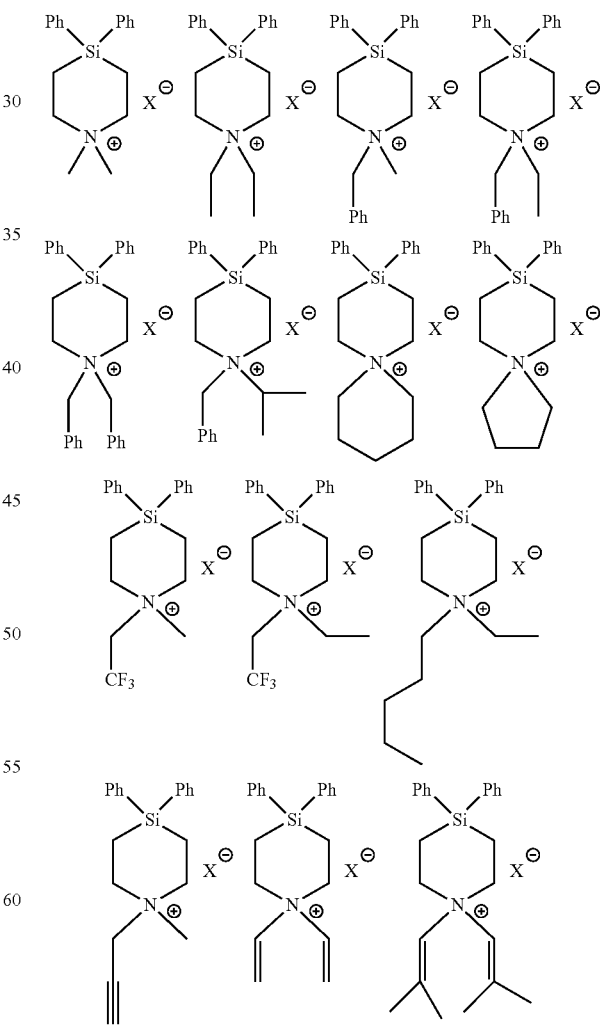

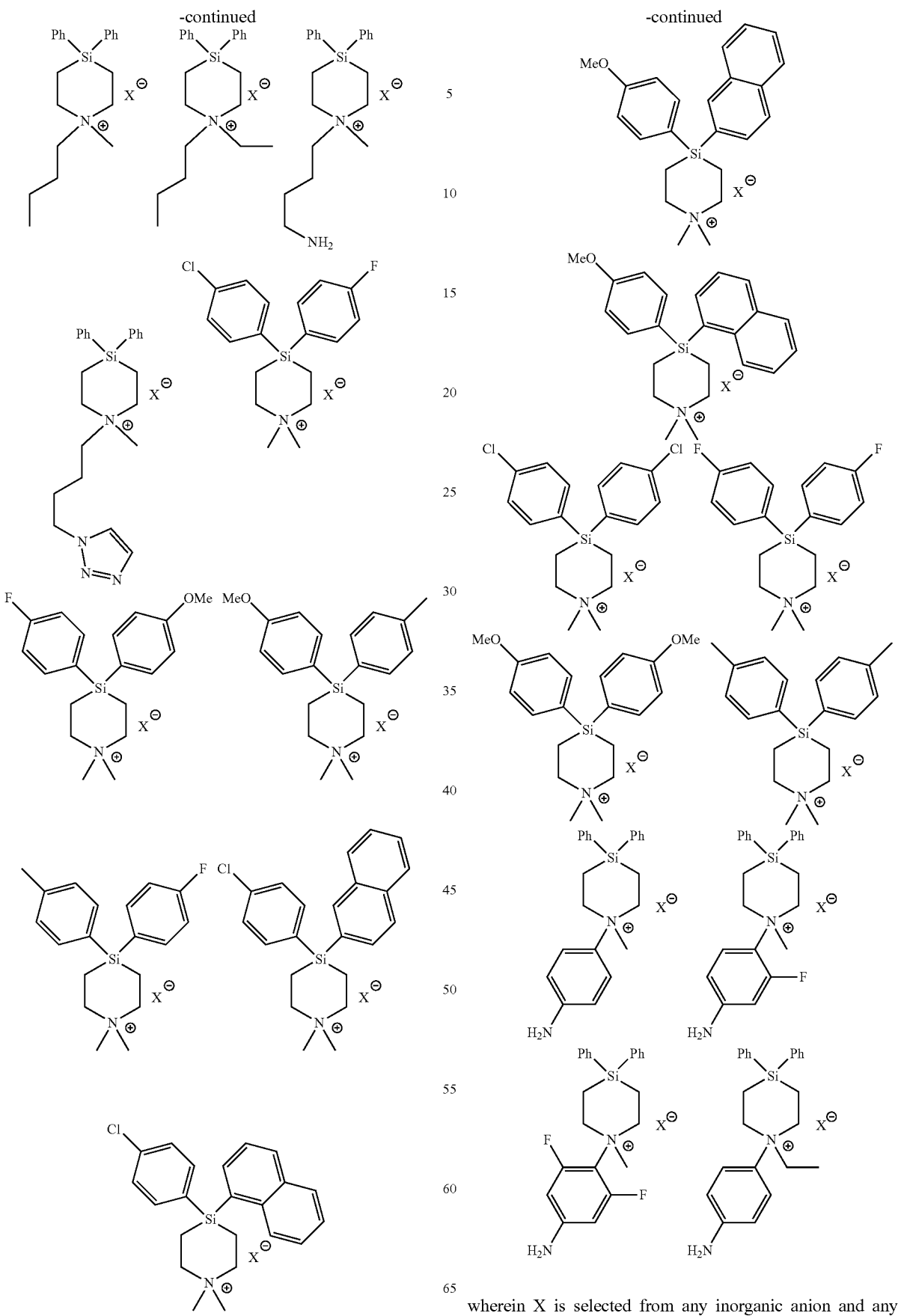
wherein X is selected from any inorganic anion and any organic anion.

5. The pharmaceutical composition as claimed in claim 2, wherein said composition comprises the compound of formula (I) or pharmaceutically acceptable salt thereof in the range of 1 to 25% by weight.

6. The pharmaceutical composition as claimed in claim 2, wherein the composition is useful as anti-malarial and anti-toxoplasma agent.

7. The pharmaceutical composition as claimed in claim 2, wherein the drug is selected from anti-malarial drug or anti-toxoplasmal drug.

8. The pharmaceutical composition as claimed in claim 2, wherein the composition is effective against pathogens selected from *Plasmodium falciparum* and *Toxoplasma gondii*.

9. The pharmaceutical composition as claimed in claim 2, wherein the composition is adapted for oral, systematic or topical administration.

10. A method of treating infections comprising administrating to a subject in need of such treatment a therapeutically effective amount of pharmaceutical composition of compound of formula I, or a geometrical isomer, analogue and/or salt thereof as claimed in claim 1, along with a carrier or diluent or pharmaceutically acceptable excipient.

11. A method for treating an infection as claimed in claim 10, wherein the infection caused by a bacteria that employs an efflux pump resistance as one of the ways of resistance, comprising administering to a patient in need thereof a therapeutically effective amount of an antibacterial agent and a compound of formula I, or a geometrical isomer, analogue and/or salt thereof.

12. The compound, or a geometrical isomer, analogue, and/or salt thereof as claimed in claim 1, wherein X is an inorganic anion selected from halide, carbonate, sulfate, and nitrate or an organic anion selected from acetate, tartrate, citrate, carbonate, and organosulfonates.

13. The compound, or a geometrical isomer, analogue, and/or salt thereof as claimed in claim 12, wherein the organosulfonates are selected from tosylate, mesylate or triflate.

14. The pharmaceutical composition as claimed in claim 2, wherein X is an inorganic anion selected from halide, carbonate, sulfate, and nitrate or an organic anion selected from acetate, tartrate, citrate, carbonate, and organosulfonates.

15. The pharmaceutical composition as claimed in claim 14, wherein the organosulfonates are selected from tosylate, mesylate or triflate.

* * * * *